United States Patent
Melese et al.

(10) Patent No.: US 6,894,055 B2
(45) Date of Patent: May 17, 2005

(54) THIENO-2',3' -5,6PYRIMIDO[3,4-A]-1,2,4-TRIAZOLE DERIVATIVES AS MODULATORS OF PHOSHOINOSITIDE 3-KINASE

(75) Inventors: Teri Melese, Cupertino, CA (US); Edward L. Perkins, Duluth, MN (US); Allen T. Q. Nguyen, Santa Clara, CA (US); Dongxu Sun, Cupertino, CA (US)

(73) Assignee: Iconix Pharmaceuticals Inc., Mountain View, CA (US)

( * ) Notice: Subject to any disclaimer, the term of this patent is extended or adjusted under 35 U.S.C. 154(b) by 0 days.

(21) Appl. No.: 10/280,138

(22) Filed: Oct. 24, 2002

(65) Prior Publication Data

US 2003/0158212 A1 Aug. 21, 2003

Related U.S. Application Data

(60) Provisional application No. 60/335,167, filed on Oct. 24, 2001.

(51) Int. Cl.$^7$ ..................... C07D 495/22; A61K 31/519
(52) U.S. Cl. ....................... 514/257; 544/247
(58) Field of Search .......................... 514/257; 544/247

(56) References Cited

PUBLICATIONS

Arya, V. P., Indian Journal of Chemistry, 10(12), 1141–50 1972.*
Ram, Vishnu J.; Pandey, Hrishi Kesh; Vlietnck, Arnold J., Journal of Heterocyclic Chemistry, 18(7), 1277–80 (English) 1981.*
Wamhoff, Heinrich; Ertas, Muemtaz, Chemiker-Zeitung, 107(11), 344–5 (German) 1983.*
Patil, C.D.; Sadana, G. S.; Deodhar, K.D., Journal of the Indian Chemical Society, 68(3), 169–71 (English) 1991.*
Moneer, A. A.; Ismail, M. Mhsen.; Osman, A. N.; El–Fattah, B. Abd; Ghoneim, K. M., Egyptian Journal of Pharmaceutical Sciences, 1993, 34(4–6), 623–41 (English) 1994.*
Ismail, Khadiga A.; Aboulwafa, Omaima M.; Koreish, Essam, Farmaco, 50(9), 611–16 (English) 1995.*
Oganisyan, A. Sh.; Noravyan, A. S.; Karapetyan, A. A.; Aleksanyan, M. S.;Struchkov, Yu. T., Chemistry of Heterocyclic Compounds, (Translation of Khimiya Geterotsiklicheskikh Soedinenii), 37(5), 628–632 (English) 2001.*
Balla, T., Curr. Pharm. Des., vol. 7(6), 2001, pp. 475–507, Medline abstract 11281854.*
Berrie, C.P., Expert Opin. Investig. Drugs, vol. 10(6), 2001, 1085–1098., Medline abstract 11772237.*

Davies et al., "Specificity and mechanism of action of some commonly used protein kinase inhibitors," *Biochem. J* 351:95–105, 2000.
Franke et al., "P13K: downstream AKTion blocks apoptosis," *Cell* 88:435–437, 1997.
Haas–Kogan et al., "Protein kinase B (PKB/Akt) activity is elevated in glioblastoma cells due to mutation of the tumor suppressor PTEN/MMAC," *Curr. Biol.* 8:1195–1198, 1998.
Leibel et al., "Radiation therapy for neoplasms of the brain," *J. Neurosurg.* 66:1–22, 1987.
Powis et al., "Wortmannin, a potent and selective inhibitor of phosphatidylinositol–3–kinase," *Cancer Res.* 54:2419–2423, 1994.
Shayesteh et al., "PIK3CA is implicated as an oncogene in ovarian cancer," *Nature Genetics* 21:99–102, 1999.
Vlahos et al., "A specific inhibitor of phosphatidylinositol 3–kinase, 2–(4–morpholinyl)–8–phemyl–4H–1–benzopyran–4–one (LY294002)," *J. Biol. Chem.* 269:5241–5248, 1994.

\* cited by examiner

*Primary Examiner*—Thomas C. MacKenzie
(74) *Attorney, Agent, or Firm*—Howrey Simon Arnold & White LLP; Adam Whiting

(57) ABSTRACT

Compounds of formula 1 are effective modulators of PI3 kinase:

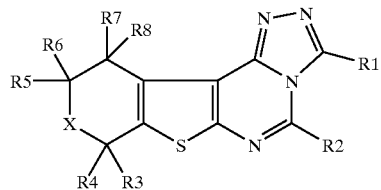

wherein X is $CR_9R_{10}$, O, $NR_{11}$ (where $R_9$ and $R_{10}$ are each independently H, lower alkyl, lower alkoxy, or halo, and $R_{11}$ is H or lower alkyl); or single bond;

$R_1$ is H, lower alkyl, aryl, aralkyl;

$R_2$ is H, lower alkyl, aryl, aralkyl, heteroaryl, heteroarylalkyl, lower alkoxy, amino, lower alkylamino, lower acylamino, arylamino, arylacyl-amino, heteroarylamino, heteroaryl-acyl amino, thio, lower alkylthio, arylthio, or aralkyl-thio, where aryl and heteroaryl are substituted with 0–3 substituents selected from the group consisting of halo, trihalomethyl, hydroxy, lower alkyl and lower alkoxy;

$R_3$, $R_4$, $R_5$, $R_6$, $R_7$, and $R_8$ are each independently H, lower alkyl, lower alkoxy, or halo;

or a pharmaceutically acceptable salt or ester thereof.

11 Claims, No Drawings

THIENO-2',3'-5,6PYRIMIDO[3,4-A]-1,2,4-TRIAZOLE DERIVATIVES AS MODULATORS OF PHOSHOINOSITIDE 3-KINASE

CROSS-REFERENCE TO RELATED APPLICATION

This application is related to provisional patent application Ser. No. 60/335,167, filed Oct. 24, 2001, from which priority is claimed under 35 USC §119(e)(1) and which is incorporated herein by reference in its entirety.

FIELD OF THE INVENTION

This invention relates generally to the fields of medicine and molecular biology. More specifically, the invention relates to compounds and methods for modulating the activity of PI3 kinase.

BACKGROUND OF THE INVENTION

The family of phosphoinositide 3-kinases ("PI3 kinase", or "PI3K") is ubiquitously expressed in cells, and their activation plays a major role in intracellular signal transduction. Activators of this enzyme include many cell surface receptors, especially those linked to tyrosine kinases. PI3K catalyzes the phosphorylation of membrane inositol lipids, with different family members producing different lipid products. Two of these products, phosphatidylinositol (3,4)-bisphosphate [PtdIns (3,4)$P_2$] and phosphatidylinositol (3,4,5)-triphosphate [PtdIns (3,4,5)$P_3$] act as "second messengers" that influence a variety of cellular processes and events.

PI3K was first identified as a heteromeric complex of two subunits: a 110 kDa catalytic subunit (p110α) and a 85 kDa regulatory subunit (p85α). Since then, eight additional PI3Ks have been identified: these are grouped into three main classes based on differences in their subunit structure and substrate preference in vitro. p110α falls into Class I, and is further categorized into Class Ia based on its mechanism of action in vivo. Two other close members in this group are p110β and p110δ. The p85 adapter subunit has two SH2 domains that allow PI3K to associate with cell surface receptors of the tyrosine kinase family, and are thereby critical to activate the enzyme, although a detailed mechanism of action is unknown.

Once PI3K is activated, it generates lipid products that act to stimulate many different cellular pathways. Many of these pathways have been described for the Class Ia group in a number of different cell types. It is evident that the cellular effects observed upon PI3K activation are the result of downstream targets of this enzyme. For example, protein kinase B (PKB) or AKT, and the related kinases protein kinases A and C (PKA and PKC) are activated by two phosphorylation events catalyzed by PDK1, an enzyme that is activated by PI3K.

A number of observations that link PI3K function with cell proliferation and inflammation point to a therapeutic role for PI3K inhibitors. In the area of oncology, results show that the p110α subunit of PI3K is amplified in ovarian tumors (L. Shayesteh et al., *Nature Genetics* (1999) 21:99–102). Further investigations have also shown that PI3K activity is elevated in ovarian cancer cell lines, and treatment with the known PI3K inhibitor LY 294002 decreases proliferation and increases apoptosis. These studies suggest that PI3K is an oncogene with an important role in ovarian cancer.

A malignant tumor of the central nervous system, glioblastoma, is highly resistant to radiation and chemotherapy treatments (S. A. Leibel et al., *J Neurosurg* (1987) 66:1–22). The PI3K signal transduction pathway inhibits apoptosis induced by cytokine withdrawal and the detachment of cells from the extracellular matrix (T. F. Franke et al., *Cell* (1997) 88:435–37). D. Haas-Kogan et al., *Curr Biol* (1998) 8:1195–98 have demonstrated that glioblastoma cells, in contrast to primary human astrocytes, have high PKB/AKT activity, and subsequently high levels of the lipid second messengers produced by PI3K activity. Addition of the known PI3K inhibitor LY 294002 reduced the levels of the lipid products and abolished the PKB/AKT activity in the glioblastoma cells. Additionally, evidence exists to support the misregulation of the PI 3-kinase-PKB pathway in these cells. The glioblastoma cells contain a mutant copy of the putative 3' phospholipid phosphatase PTEN. This phosphatase normally removes the phosphate group from the lipid product, thus acting to regulate signaling through the PI3K pathways. When wild-type PTEN was expressed in the tumor cells PKB/AKT activity was abolished. These experiments suggest a role for PTEN in regulating the activity of the PI3K pathway in malignant human cells. In further work these investigators also observed that inhibition of PDK1 reduced PKB/AKT activity. PDK1, as described above, is a protein kinase activated by PI3K, and is likely responsible for inducing the events that lead to the activation of PKB/AKT activity. In addition, cell survival was dramatically reduced following treatment with antisense oligonucleotides against PDK1. Thus inhibitors of the PI3K pathway including PI 3-kinase, PDK1, and PKB/AKT are all potential targets for therapeutic intervention for glioblastoma.

Another potential area of therapeutic intervention for inhibitors of PI3K is juvenile myelomonocytic leukemia. The NF1 gene encodes the protein neurofibromin, a GTPase activating ("GAP") protein for the small GTPase Ras. Immortalized immature myelomonocytic cells from NF1 −/− mice have been generated that have deregulated signaling through the Ras pathway, including the PI3K/PKB pathway. These cells undergo apoptosis when incubated with known inhibitors of PI3K, LY294002 and wortmannin, indicating a normal role for the protein in cell survival.

Wortmannin (G. Powis et al., *Cancer Res* (1994) 54:2419–23) was originally isolated from soil bacteria, while LY294002 (C. J. Vlahos et al., *J Biol Chem* (1994) 269:5241–48) is a derivative of the broad spectrum kinase inhibitor quercetin. The site of action of both inhibitors is the ATP-binding site. While wortmannin has an $IC_{50}$ of 2–5 nM, the $IC_{50}$ for LY294002 is 0.5–1.5 μM on purified PI3K. Extensive testing of these and other kinase inhibitors has shown that both are effective inhibitors of other unrelated enzymes with similar affinities (S. P. Davies et al., *Biochem J* (2000) 351:95–105). Further, neither inhibitor is isoform-specific on PI3K, and the therapeutic index is low, indicating that these two inhibitors have low pharmaceutical potential. However, the clear clinical significance of developing a selective PI3K inhibitor, both in oncology and inflammation, coupled with the inability of presently known inhibitors to show selectivity, indicates a pressing need for novel PI3K inhibitors.

SUMMARY OF THE INVENTION

One aspect of the invention is a compound of formula 1:

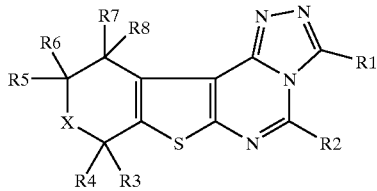

wherein X is $CR_9R_{10}$, O, $NR_{11}$, or single bond, where $R_9$ and $R_{10}$ are each independently H, lower alkyl, lower alkoxy, or halo, and $R_{11}$ is H or lower alkyl; $R_1$ is H, lower alkyl, aryl, or aralkyl; $R_2$ is H, lower alkyl, aryl, aralkyl, heteroaryl, heteroaryl-alkyl, lower alkoxy, amino, lower alkylamino, lower acylamino, arylamino, arylacyl-amino, heteroaryl-amino, hetero-aryl-acyl amino, thio, lower alkylthio, arylthio, or aralkyl-thio, where aryl and heteroaryl are substituted with 0–3 substituents selected from the group consisting of halo, trihalomethyl, hydroxy, lower alkyl and lower alkoxy; $R_3$, $R_4$, $R_5$, $R_6$, $R_7$, and $R_8$ are each independently H, lower alkyl, lower alkoxy, or halo; and pharmaceutically acceptable salts thereof.

Another aspect of the invention is the method of inhibiting PI3 kinase by contacting the enzyme with an effective amount of a compound of formula 1.

Another aspect of the invention is a method for treating a subject having a PI3K-mediated disorder, comprising administering an effective amount of a compound of formula 1 in a pharmaceutically acceptable carrier.

Another aspect of the invention is a composition comprising an effective amount of a compound of formula 1, and a pharmaceutically acceptable excipient.

DETAILED DESCRIPTION

Definitions:

The terms "compound of formula 1" and "compound of the invention" refer to compounds having the structure:

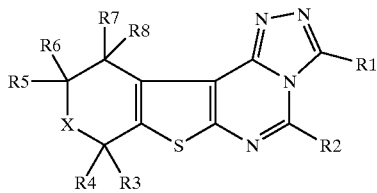

wherein X is $CR_9R_{10}$, O, $NR_{11}$, or a direct bond, where $R_9$ and $R_{10}$ are each independently H, lower alkyl, lower alkoxy, or halo, and $R_{11}$ is H or lower alkyl; $R_1$ is H, lower alkyl, aryl, or aralkyl; $R_2$ is H, lower alkyl, aryl, aralkyl, heteroaryl, heteroaryl-alkyl, lower alkoxy, amino, lower alkylamino, lower acylamino, arylamino, arylacyl-amino, heteroaryl-amino, hetero-aryl-acyl amino, thio, lower alkylthio, arylthio, or aralkyl-thio, where aryl and heteroaryl are substituted with 0–3 substituents selected from the group consisting of halo, trihalomethyl, hydroxy, lower alkyl and lower alkoxy; $R_3$, $R_4$, $R_5$, $R_6$, $R_7$, and $R_8$ are each independently H, lower alkyl, lower alkoxy, or halo; and pharmaceutically acceptable salts thereof. Compounds of the inven tion are named as cycloalkanothieno[2',3'-5,6]pyrimido[3,4-a]-1,2,4-triazoles, and are numbered as follows:

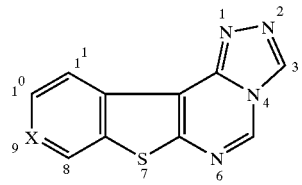

Compounds of the invention in which X is $NR_{11}$ or O are named as piperido[3",4"-4',5']thieno[2',3'-5,6]pyrimido[3,4-a]-1,2,4-triazoles and tetrahydropyrano[3",4"-4',5']thieno-[2',3'-5,6]pyrimido[3,4-a]-1,2,4-triazoles, respectively.

The term "lower alkyl" refers to radicals containing carbon and hydrogen, without unsaturation, having from one to six carbon atoms, inclusive. Lower alkyl radicals can be straight or branched. Exemplary lower alkyl radicals include, without limitation, methyl, ethyl, propyl, isopropyl, hexyl, t-butyl, and the like. The term "cycloalkyl" refers to alkyl radicals having 3–10 carbon atoms and containing at least one ring. Exemplary cycloalkyl radicals include, without limitation, cyclopropyl, cyclobutyl, cyclopentyl, cyclohexyl, 2-methylcyclopropyl, 2,6-dimethylcyclohexyl, and the like. The term "lower alkenyl" refers to a hydrocarbon radical having 2–6 carbon atoms, and at least one double bond. Exemplary lower alkenyl radicals include, without limitation, vinyl, propenyl, butenyl, and the like. The term "lower alkynyl" refers to a hydrocarbon radical having 2–6 carbon atoms, and at least one triple bond. Exemplary lower alkynyl radicals include, without limitation, ethynyl, propynyl, butynyl, and the like.

"Lower alkoxy" refers to a radical of the form RO—, where R is lower alkyl as defined above. Suitable lower alkoxy radicals include, without limitation, methoxy, ethoxy, propoxy, t-butoxy, and the like. Similarly, "lower alkylamino" refers to a radical of the form RNH—, where R is lower alkyl. The term "lower alkylenedioxy" refers to a group of the form —ORO—, where R is a hydrocarbon diradical of 1–6 carbon atoms. Exemplary lower alkylenedioxy groups include, without limitation, methylenedioxy, ethylenedioxy, 1,1-dimethylmethylenedioxy, and the like. The term "lower alkylthio" refers to a group of the form RS—, where R is lower alkyl as set forth above. The term "lower acyl" refers to a group of the form RC(=O)—, while "lower acyloxy" refers to a group of the form RC(=O)O—, where R is lower alkyl. The term "lower acylamino" refers to a substituent of the form RC(=O)N—, where R is lower alkyl.

The term "aryl" refers to an aromatic carbocyclic or heterocyclic moiety, having one, two, or three rings. Exemplary aryl radicals include, without limitation, phenyl, naphthyl, pyridyl, pyrimidyl, triazyl, quinazolinyl, pyranyl, thiazolyl, and the like. The terms "aralkyl" and "aryl-lower alkyl" refer to an aryl moiety joined to a lower alkyl moiety, for example benzyl, phenethyl, 2-phenylpropyl, naphthylmethyl, and the like. The term "aryloxy" refers to a group of the form ArO—, where Ar is aryl as defined above. The term "aryl acyl" refers to a group of the form ArC(=O)—, where Ar is aryl or aralkyl as defined above. The term "arylamino" refers to a group of the form ArNH—, where Ar is aryl or aralkyl as defined above.

The term "heterocyclyl" refers to a saturated or unsaturated radical having 1–4 rings and containing 1–4 heteroatoms selected from oxygen, nitrogen, sulfur, and phosphorus. Exemplary heterocyclyl radicals include, without limitation, oxiranyl, aziridinyl, thienyl, pyrrolyl, imidazolyl, pyrazolyl, pyridyl, furyl, pyranyl, pyrazinyl, indolyl, quinazolinyl, thiozolyl, isoxazolyl, piperazinyl, morpholinyl, triazolyl, oxatriazolyl, oxathiazinyl, purinyl, and the like. The term "heterocyclyl acyl" refers to a radical of the form HetC(=O)—, where Het is heterocyclyl as defined above.

The term "halo" refers to fluoro, chloro, bromo, and iodo.

The term "leaving group" refers to a radical that is easily displaced by a nucleophile in an $S_N2$ displacement reaction, or are easily eliminated in a condensation or cyclization reaction. Exemplary leaving groups include, without limitation, sulfonates such as tosylate and mesylate, silanes such as t-butyl-dimethylsilane, halogens such as bromo and chloro, and the like.

The term "pharmaceutically acceptable salts and esters" refers to derivatives of compounds of formula 1 obtained by addition of an acid or base to the compound, or condensation with an alcohol or carboxylic acid to form an ester. In either case, the acid, base, alcohol, or carboxylic acid must not be unacceptably toxic at the concentrations at which the compound is administered. Suitable acids include, without limitation, inorganic acids such as hydrochloric acid, hydrobromic acid, sulfuric acid, nitric acid or phosphoric acid; organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The term "modulate" as used herein refers to an alteration in PI3 kinase activity, and includes both increases and decreases in activity. In most cases, a compound of the invention will inhibit or decrease the protease (PI3K) activity. An "effective amount" of a compound of the invention is that quantity or concentration necessary to effect a measurable change in the protease activity. The threshold change is a change that is statistically significant, and/or at least 10%.

The term "subject" as used herein refers to a bird or mammal that expresses PI3 kinase. Exemplary subjects include birds such as chickens, ducks, geese, turkeys, and other wild and domestic fowl and the like; and mammals including, without limitation, cattle, pigs, humans, apes, mice, rats, guinea pigs, and the like. A "therapeutic amount" of a compound of the invention is that quantity which is sufficient for treatment of the disorder. The therapeutic amount can be divided into a plurality of individual doses that may be ineffective individually, but are effective when taken in the quantity necessary. "Treatment" can comprise: reduction or elimination of symptoms, prevention of an increase in symptoms, acceleration of recovery time, prevention of symptoms (prophylaxis), and the like. The exact quantity comprising a therapeutic amount can vary depending on the species of the subject, its size, weight, age, condition, degree of the disorder, the presence of additional infections or disorders, and the like. However, the therapeutic amount can be established by routine experimentation using known methods.

The term "pharmaceutically acceptable excipient" refers to a carrier that does not interfere with the activity of a compound of the invention upon administration, and is not unacceptably toxic to the subject to which it is administered, in the amount in which it is administered.

General Method

The compounds of this invention are prepared by several routes as shown in the reaction schemes below. Additional information is available from the following references: Progress in Heterocyclic Chemistry (Volumes 1 to 12); Pergamon Press, NY, N.Y. "The Chemistry of Amidines and Imidates" (ed. S. Pata; Wiley Interscience Press, NY, N.Y., 1975); "Protecting Groups in Organic Synthesis", (P. Wuts and T. Greene, Wiley Publishers, NY, N.Y. 1995); M. Robba, et al., J. Heterocyclic Chem. (1975) 12:525–27; C. J. Shishoo, et al., J. Heterocyclic Chem (1981) 18:43–46; C. J. Shishoo, et al., J. Heterocyclic Chem. (1987) 24:1125–31 (1987); and K. Gewald, Chem. Ber. (1965) 98:3571.

In Scheme 1, an α-halo-cyclohexanone ("Compound A") is treated with di-cyano-methane in a strong base (for example, triethyl amine) to provide intermediate Compound B. Compound B is then cyclized by reaction with NaSH in ethanol, yielding Compound C. This intermediate is then treated with acid (for example aqueous $H_2SO_4$), followed by amidine $R_2C(=NH)NH_2$ to provide Compound D, which is chlorinated with $POCl_3$—$PCL_5$ to yield chloropyrimidine derivative Compound E. Compound E can be converted to hydrazine derivative Compound F by treatment with hydrazine, then cyclized to Compound G by condensation with an orthoester of the form $R_1C(OEt)_3$. Alternatively, Compound E can be converted directly to Compound G by treatment with $R_1CONHNH_2$.

Scheme 1:

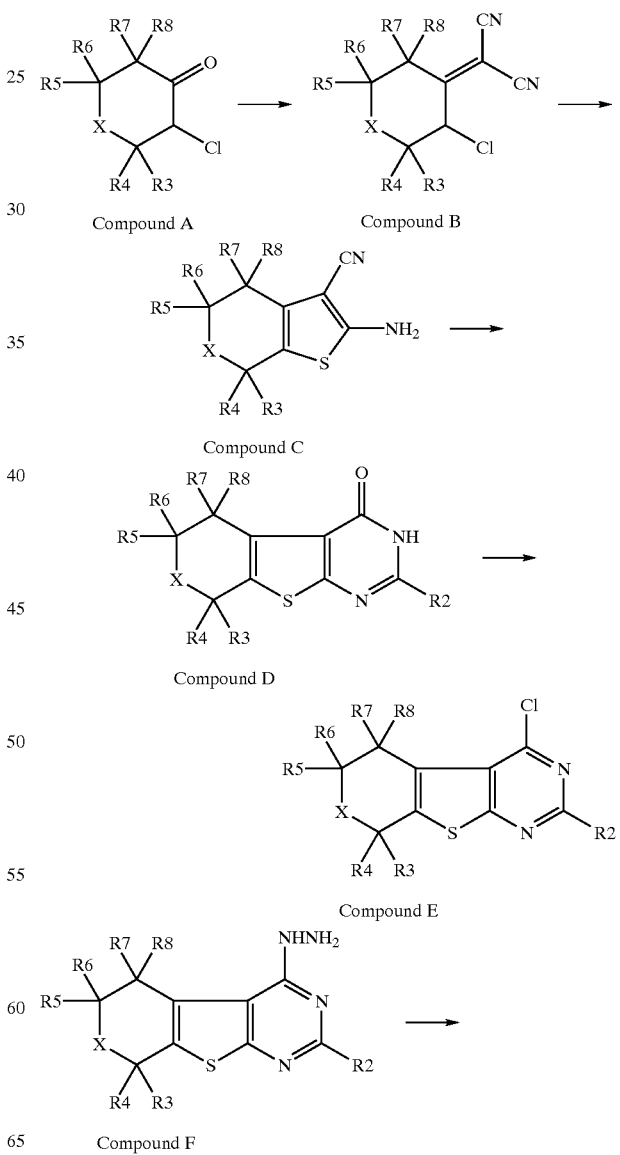

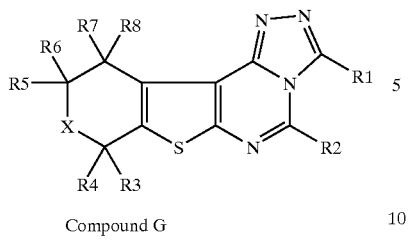

Compound G

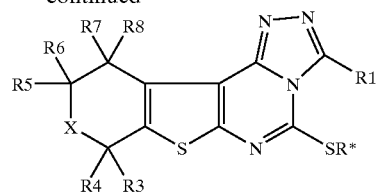

Compound L

Scheme 2 can be used to provide compounds of the invention wherein R₂ is thio, lower alkylthio, arylthio, or aralkyl-thio. In Scheme 2, a compound of formula C is treated with H₂S, pyridine, and NEt₃ to provide thioamide derivative Compound H. This intermediate is then treated with methyl iodide or SO₂(OMe)₂, followed by NH₂NHCOR₁ or NH₂NHCSR₁ and heat to provide the triazole derivative Compound J. Compound J is then cyclized by adding C(=S)Cl₂ or thiocarbonyldiimidazole to provide Compound K, which is then substituted by treatment with R*I and base, where –SR* is R₂.

Scheme 2:

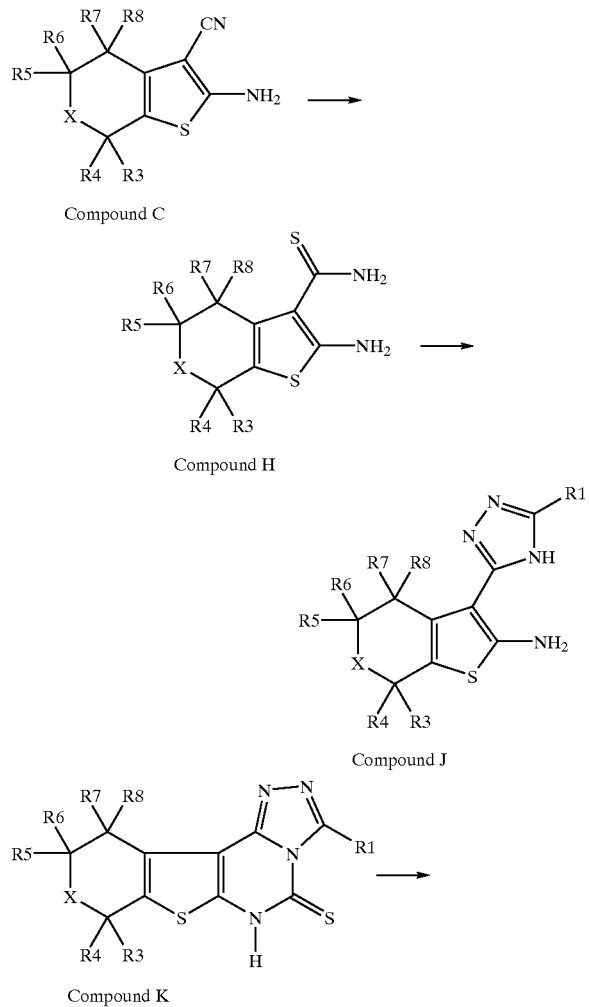

Candidate compounds of the invention can be tested for activity by any acceptable means, for example using the methods set forth in the Examples below.

Compounds of the invention can be administered to a subject, or can be applied directly to cells, for example in a cell culture. If administered to a cell culture, the compound is preferably first suspended or dissolved in a suitable carrier. Suitable carriers include, without limitation, water, saline solution, dimethylsulfoxide (DMSO) and solutions thereof, cell culture media, and the like. Alternatively, compounds of the invention can be applied directly to PI3K to inhibit its activity in vitro, for example as a positive control during drug screening.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

A compound of formula 1 or a pharmaceutical composition containing same is administered via any of the usual and acceptable methods known in the art, either singly or in combination with another compound or compounds of the present invention or other pharmaceutical agents. These compounds or compositions can thus be administered orally, systemically (e.g., transdermally, intranasally or by suppository) or parenterally (e.g., intramuscularly, subcutaneously and intravenously), and can be administered either in the form of solid or liquid dosages including tablets, solutions, suspensions, aerosols, and the like, as discussed in more detail above. It is preferred to administer compounds of formula 1 orally. The formulation can be administered in a single unit dosage form for continuous treatment or in a single unit dosage form ad libitum when relief of symptoms is specifically required.

EXAMPLES

The following examples are provided as a guide for the practitioner of ordinary skill in the art. Nothing in the examples is intended to limit the claimed invention. Unless otherwise specified, all reagents are used in accordance with the manufacturer's recommendations, and all reactions are performed at standard temperature and pressure.

Example 1

Synthesis of Compounds (A) A solution of 2-chlorocyclohexanone is treated with dicyanomethane in triethylamine to provide 1-dicyanomethylidienyl-2-chlorocyclohexane (Compound B). Compound B is treated with NaSH in EtOH to provide 2-amino-3-cyano-cyclohexothiophene (Compound C). Compound C is treated with aqueous $H_2SO_4$, followed by 3-pyridylamidine to provide cyclohexothiophenopyrimidinone derivative Compound D ($R_2$=3-pyridyl). Compound D is then chlorinated with $POCl_3+PCl_5$ to provide the chloropyrimidine derivative Compound E. Compound E is treated with hydrazine to provide hydrazo derivative Compound F, which is then allowed to react with triethoxymethane (orthoformic acid triethyl ester) to yield 5-(3-pyridyl)-cyclohexothieno[2',3'-5,6]pyrimido[3,4-a]-1,2,4-triazole (Compound G).

(B) Similarly, proceeding as in part (A) above, but substituting 3-chloro-5-methyl-piperidin-4-one, 2,2-dimethyl-5-chloro-1,4-tetrahydropyrone, and 2-chloro-4,5-dimethoxy-cyclohexanone for 2-chlorocyclohexanone, the following compounds are prepared:

5-(3-pyridyl)-piperido[3",4"-4',5']thieno[2',3'-5,6]pyrimido[3,4-a]-1,2,4-triazole;

5-(3-pyridyl)-10,10-dimethyl-tetrahydropyrano[3",4"-4',5']thieno[2',3'-5,6]pyrimido[3,4-a]-1,2,4-triazole; and 5-(3-pyridyl)-9,10-dimethoxy-cyclohexothieno[2',3'-5,6]pyrimido[3,4-a]-1,2,4-triazole.

(C) Proceeding as in parts (A) and (B) above, but substituting butyramidine, phenacetamidine, and cyclohexyl-amidine for 3-pyridyl-amidine, the following compounds are prepared:

5-butyl-cyclohexothieno[2',3'-5,6]pyrimido[3,4-a]-1,2,4-triazole;

5-butyl-piperido[3",4"-4',5']thieno[2',3'-5,6]pyrimido[3,4-a]-1,2,4-triazole;

5-butyl-10,10-dimethyl-tetrahydropyrano[3",4"-4',5']thieno[2',3'-5,6]pyrimido[3,4-a]-1,2,4-triazole;

5-butyl-9,10-dimethoxy-cyclohexothieno[2',3'-5,6]pyrimido[3,4-a]-1,2,4-triazole;

5-benzyl-cyclohexothieno[2',3'-5,6]pyrimido[3,4-a]-1,2,4-triazole;

5-benzyl-piperido[3",4"-4',5']thieno[2',3'-5,6]pyrimido[3,4-a]-1,2,4-triazole;

5-benzyl-10,10-dimethyl-tetrahydropyrano[3",4"-4',5']thieno[2',3'-5,6]pyrimido[3,4-a]-1,2,4-triazole;

5-benzyl-9,10-dimethoxy-cyclohexothieno[2',3'-5,6]pyrimido[3,4-a]-1,2,4-triazole;

5-cyclohexyl-cyclohexothieno[2',3'-5,6]pyrimido[3,4-a]-1,2,4-triazole;

5-cyclohexyl-piperido[3",4"-4',5']thieno[2',3'-5,6]pyrimido[3,4-a]-1,2,4-triazole;

5-cyclohexyl-10,10-dimethyl-tetrahydropyrano[3",4"-4',5']thieno[2',3'-5,6]pyrimido[3,4-a]-1,2,4-triazole; and 5-cyclohexyl-9,10-dimethoxy-cyclohexothieno[2',3'-5,6]pyrimido[3,4-a]-1,2,4-triazole.

(D) Proceeding as in parts (A)–(C) above, but substituting 1,1,1-triethoxy-ethane (orthoacetic acid triethyl ester), 1,1,1-triethoxy-2-methylpropane, (triethoxymethyl)benzene, and 2,2,2-triethoxy-ethylbenzene for triethoxymethane, the following compounds are prepared:

3-methyl-5-(3-pyridyl)-cyclohexothieno[2',3'-5,6]pyrimido[3,4-a]-1,2,4-triazole;

3-methyl-5-(3-pyridyl)-piperido[3",4"-4',5']thieno[2',3'-5,6]pyrimido[3,4-a]-1,2,4-triazole;

3-methyl-5-(3-pyridyl)-10,10-dimethyl-tetrahydropyrano[3",4"-4',5']thieno[2',3'-5,6]pyrimido[3,4-a]-1,2,4-triazole;

3-methyl-5-(3-pyridyl)-9,10-dimethoxy-cyclohexothieno[2',3'-5,6]pyrimido[3,4-a]-1,2,4-triazole;

3-methyl-5-butyl-cyclohexothieno[2',3'-5,6]pyrimido[3,4-a]-1,2,4-triazole;

3-methyl-5-butyl-piperido[3",4"-4',5']thieno[2',3'-5,6]pyrimido[3,4-a]-1,2,4-triazole;

3-methyl-5-butyl-10,10-dimethyl-tetrahydropyrano[3",4"-4',5']thieno[2',3'-5,6]pyrimido[3,4-a]-1,2,4-triazole;

3-methyl-5-butyl-9,10-dimethoxy-cyclohexothieno[2',3'-5,6]pyrimido[3,4-a]-1,2,4-triazole;

3-methyl-5-benzyl-cyclohexothieno[2',3'-5,6]pyrimido[3,4-a]-1,2,4-triazole;

3-methyl-5-benzyl-piperido[3",4"-4',5']thieno[2',3'-5,6]pyrimido[3,4-a]-1,2,4-triazole;

3-methyl-5-benzyl-10,10-dimethyl-tetrahydropyrano[3",4"-4',5']thieno[2',3'-5,6]pyrimido[3,4-a]-1,2,4-triazole;

3-methyl-5-benzyl-9,10-dimethoxy-cyclohexothieno[2',3'-5,6]pyrimido[3,4-a]-1,2,4-triazole;

3-methyl-5-cyclohexyl-cyclohexothieno[2',3'-5,6]pyrimido[3,4-a]-1,2,4-triazole;

3-methyl-5-cyclohexyl-piperido[3",4"-4',5']thieno[2',3'-5,6]pyrimido[3,4-a]-1,2,4-triazole;

3-methyl-5-cyclohexyl-10,10-dimethyl-tetrahydropyrano[3",4"-4',5 ']thieno[2',3'-5,6]pyrimido[3,4-a]-1,2,4-triazole;

3-methyl-5-cyclohexyl-9,10-dimethoxy-cyclohexothieno[2',3'-5,6]pyrimido[3,4-a]-1,2,4-triazole;

3-isopropyl-5-(3-pyridyl)-cyclohexothieno[2',3'-5,6]pyrimido[3,4-a]-1,2,4-triazole;

3-isopropyl-5-(3-pyridyl)-piperido[3",4"-4',5']thieno[2',3'-5,6]pyrimido[3,4-a]-1,2,4-triazole;

3-isopropyl-5-(3-pyridyl)-10,10-dimethyl-tetrahydropyrano[3",4"-4',5']thieno[2',3'-5,6]pyrimido[3,4-a]-1,2,4-triazole;

3-isopropyl-5-(3-pyridyl)-9,10-dimethoxy-cyclohexothieno[2',3'-5,6]pyrimido[3,4a]-1,2,4-triazole;

3-isopropyl-5-butyl-cyclohexothieno[2',3'-5,6]pyrimido[3,4-a]-1,2,4-triazole;

3-isopropyl-5-butyl-piperido[3",4"-4',5']thieno[2',3'-5,6]pyrimido[3,4-a]-1,2,4-triazole;

3-isopropyl-5-butyl-10,10-dimethyl-tetrahydropyrano[3",4"-4',5']thieno[2',3'-5,6]pyrimido[3,4-a]-1,2,4-triazole;

3-isopropyl-5-butyl-9,10-dimethoxy-cyclohexothieno[2',3'-5,6]pyrimido[3,4-a]-1,2,4-triazole;

3-isopropyl-5-benzyl-cyclohexothieno[2',3'-5,6]pyrimido[3,4-a]-1,2,4-triazole;

3-isopropyl-5-benzyl-piperido[3",4"-4',5']thieno[2',3'-5,6]pyrimido[3,4-a]-1,2,4-triazole;

3-isopropyl-5-benzyl-10,10-dimethyl-tetrahydropyrano[3",4"-4',5']thieno[2',3'-5,6]pyrimido[3,4-a]-1,2,4-triazole;

3-isopropyl-5-benzyl-9,10-dimethoxy-cyclohexothieno[2',3'-5,6]pyrimido[3,4-a]-1,2,4-triazole;

3-isopropyl-5-cyclohexyl-cyclohexothieno[2',3'-5,6]pyrimido[3,4-a]-1,2,4-triazole;

3-isopropyl-5-cyclohexyl-piperido[3",4"-4',5']thieno[2',3'-5,6]pyrimido[3,4-a]-1,2,4-triazole;

3-isopropyl-5-cyclohexyl-10,10-dimethyl-tetrahydropyrano[3",4"-4',5']thieno[2',3'-5,6]pyrimido[3,4-a]-1,2,4-triazole;

3-isopropyl-5-cyclohexyl-9,10-dimethoxy-cyclohexothieno[2',3'-5,6]pyrimido[3,4-a]-1,2,4-triazole;

3-phenyl-5-(3-pyridyl)-cyclohexothieno[2',3'-5,6]pyrimido[3,4-a]-1,2,4-triazole;

3-phenyl-5-(3-pyridyl)-piperido[3",4"-4',5']thieno[2',3'-5,6]pyrimido[3,4-a]-1,2,4-triazole;

3-phenyl-5-(3-pyridyl)-10,10-dimethyl-tetrahydropyrano[3",4"-4',5']thieno[2',3'-5,6]pyrimido[3,4-a]-1,2,4-triazole;

3-phenyl-5-(3-pyridyl)-9,10-dimethoxy-cyclohexothieno[2',3'-5,6]pyrimido[3,4-a]-1,2,4-triazole;

3-phenyl-5-butyl-cyclohexothieno[2',3'-5,6]pyrimido[3,4-a]-1,2,4-triazole;

3-phenyl-5-butyl-piperido[3",4"-4',5']thieno[2',3'-5,6]pyrimido[3,4-a]-1,2,4-triazole;

3-phenyl-5-butyl-10,10-dimethyl-tetrahydropyrano[3",4"-4',5']thieno[2',3'-5,6]pyrimido[3,4-a]-1,2,4-triazole;

3-phenyl-5-butyl-9,10-dimethoxy-cyclohexothieno[2',3'-5,6]pyrimido[3,4-a]-1,2,4-triazole;

3-phenyl-5-benzyl-cyclohexothieno[2',3'-5,6]pyrimido[3,4-a]-1,2,4-triazole;

3-phenyl-5-benzyl-piperido[3",4"-4',5']thieno[2',3'-5,6]pyrimido[3,4-a]-1,2,4-triazole;

3-phenyl-5-benzyl-10,10-dimethyl-tetrahydropyrano[3",4"-4',5']thieno[2',3'-5,6]pyrimido[3,4-a]-1,2,4-triazole;

3-phenyl-5-benzyl-9,10-dimethoxy-cyclohexothieno[2',3'-5,6]pyrimido[3,4-a]-1,2,4-triazole;

3-phenyl-5-cyclohexyl-cyclohexothieno[2',3'-5,6]pyrimido[3,4-a]-1,2,4-triazole;

3-phenyl-5-cyclohexyl-piperido[3",4"-4',5']thieno[2',3'-5,6]pyrimido[3,4-a]-1,2,4-triazole;

3-phenyl-5-cyclohexyl-10,10-dimethyl-tetrahydropyrano[3",4"-4',5']thieno[2',3'-5,6]pyrimido[3,4-a]-1,2,4-triazole;

3-phenyl-5-cyclohexyl-9,10-dimethoxy-cyclohexothieno[2',3'-5,6]pyrimido[3,4-a]-1,2,4-triazole;

3-benzyl-5-(3-pyridyl)-cyclohexothieno[2',3'-5,6]pyrimido[3,4-a]-1,2,4-triazole;

3-benzyl-5-(3-pyridyl)-piperido[3",4"-4',5']thieno[2',3'-5,6]pyrimido[3,4-a]-1,2,4-triazole;

3-benzyl-5-(3-pyridyl)-10,10-dimethyl-tetrahydropyrano[3",4"-4',5']thieno[2',3'-5,6]pyrimido[3,4-a]-1,2,4-triazole;

3-benzyl-5-(3-pyridyl)-9,10-dimethoxy-cyclohexothieno[2',3'-5,6]pyrimido[3,4-a]-1,2,4-triazole;

3-benzyl-5-butyl-cyclohexothieno[2',3'-5,6]pyrimido[3,4-a]-1,2,4-triazole;

3-benzyl-5-butyl-piperido[3",4"-4',5']thieno[2',3'-5,6]pyrimido[3,4-a]-1,2,4-triazole;

3-benzyl-5-butyl-10,10-dimethyl-tetrahydropyrano[3",4"-4',5']thieno[2',3'-5,6]pyrimido[3,4-a]-1,2,4-triazole;

3-benzyl-5-butyl-9,10-dimethoxy-cyclohexothieno[2',3'-5,6]pyrimido[3,4-a]-1,2,4-triazole;

3-benzyl-5-benzyl-cyclohexothieno[2',3'-5,6]pyrimido[3,4-a]-1,2,4-triazole;

3-benzyl-5-benzyl-piperido[3",4"-4',5']thieno[2',3'-5,6]pyrimido[3,4-a]-1,2,4-triazole;

3-benzyl-5-benzyl-10,10-dimethyl-tetrahydropyrano[3",4"-4',5']thieno[2',3'-5,6]pyrimido[3,4-a]-1,2,4-triazole;

3-benzyl-5-benzyl-9,10-dimethoxy-cyclohexothieno[2',3'-5,6]pyrimido[3,4-a]-1,2,4-triazole;

3-benzyl-5-cyclohexyl-cyclohexothieno[2',3'-5,6]pyrimido[3,4-a]-1,2,4-triazole;

3-benzyl-5-cyclohexyl-piperido[3",4"-4',5']thieno[2',3'-5,6]pyrimido[3,4-a]-1,2,4-triazole;

3-benzyl-5-cyclohexyl-10,10-dimethyl-tetrahydropyrano[3",4"-4',5']thieno[2',3'-5,6]pyrimido[3,4-a]-1,2,4-triazole; and 3-benzyl-5-cyclohexyl-9,10-dimethoxy-cyclohexothieno[2',3'-5,6]pyrimido[3,4-a]-1,2,4-triazole.

(E) A solution of 2-amino-3-cyano-cyclohexothiophene (Compound C) in pyridine is treated with $H_2S$ to provide 2-amino-3-thiocarbamyl-cyclohexothiophene (Compound H). Compound H is treated with $CH_3I$, followed by heating with acetyl-hydrazine to provide 2-amino-3-(5-methyl-1,2,4-triazin-3-yl)-cyclohexothiophene (Compound J). Compound J is cyclized using thionyl chloride to form Compound K, and alkylated with methyl iodide in triethylamine to provide 3-methyl-5-(methylthio)-cyclohexothieno[2',3'-5,6]pyrimido[3,4-a]-1,2,4-triazole.

(F) Proceeding as in parts (A), (B), and (E) above, the following compounds are prepared:

3-methyl-5-methylthio-piperido[3",4"-4',5']thieno[2',3'-5,6]pyrimido[3,4-a]-1,2,4-triazole;

3-methyl-5-methylthio-10,10-dimethyl-tetrahydropyrano[3",4"-4',5']thieno[2',3'-5,6]pyrimido[3,4-a]-1,2,4-triazole; and 3-methyl-5-methylthio-9,10-dimethoxy-cyclohexothieno[2',3'-5,6]pyrimido[3,4-a]-1,2,4-triazole.

(G) Proceeding as in parts (A)–(B) and (E)–(F) above, but substituting formyl-hydrazine, 2-methylpropanoyl-hydrazine, and benzoyl-hydrazine for acetyl-hydrazine, the following compounds are prepared:

5-methylthio-cyclohexothieno[2',3'-5,6]pyrimido[3,4-a]-1,2,4-triazole;

5-methylthio-piperido[3",4"-4',5']thieno[2',3'-5,6]pyrimido[3,4-a]-1,2,4triazole;

5-methylthio-10,10-dimethyl-tetrahydropyrano[3",4"-4',5']thieno[2',3'-5,6]pyrimido[3,4-a]-1,2,4-triazole;

5-methylthio-9,10-dimethoxy-cyclohexothieno[2',3'-5,6]pyrimido[3,4-a]-1,2,4-triazole;

3-isopropyl-5-(methylthio)-cyclohexothieno[2',3'-5,6]pyrimido[3,4-a]-1,2,4-triazole;

3-isopropyl-5-methylthio-piperido[3",4"-4',5']thieno[2',3'-5,6]pyrimido[3,4-a]-1,2,4-triazole;

3-isopropyl-5-methylthio-10,10-dimethyl-tetrahydropyrano[3",4"-4',5']thieno[2',3'-5,6]pyrimido[3,4-a]-1,2,4-triazole;

3-isopropyl-5-methylthio-9,10-dimethoxy-cyclohexothieno[2',3'-5,6]pyrimido[3,4-a]-1,2,4-triazole;

3-phenyl-5-(methylthio)-cyclohexothieno[2',3'-5,6]pyrimido[3,4-a]-1,2,4-triazole;

3-phenyl-5-methylthio-piperido[3",4"-4',5']thieno[2',3'-5,6]pyrimido[3,4-a]-1,2,4-triazole;

3-phenyl-5-methylthio-10,10-dimethyl-tetrahydropyrano[3",4"-4',5']thieno[2',3'-5,6]pyrimido[3,4-a]-1,2,4-triazole; and 3-phenyl-5-methylthio-9,10-dimethoxy-cyclohexothieno[2',3'-5,6]pyrimido[3,4-a]-1,2,4-triazole.

(H) Proceeding as in parts (E) and (G) above, but substituting ethyl iodide, butyl iodide, and benzyl iodide for methyl iodide, the following compounds are prepared:

3-methyl-5-ethylthio-cyclohexothieno[2',3'-5,6]pyrimido[3,4-a]-1,2,4-triazole;

3-methyl-5-ethylthio-piperido[3",4"-4',5']thieno[2',3'-5,6]pyrimido[3,4-a]-1,2,4-triazole;

3-methyl-5-ethylthio-10,10-dimethyl-tetrahydropyrano[3",4"-4',5']thieno[2',3'-5,6]pyrimido[3,4-a]-1,2,4-triazole;

3-methyl-5-ethylthio-9,10-dimethoxy-cyclohexothieno[2',3'-5,6]pyrimido[3,4-a]-1,2,4-triazole;

5-ethylthio-cyclohexothieno[2',3'-5,6]pyrimido[3,4-a]-1,2,4-triazole;

5-ethylthio-piperido[3",4"-4',5']thieno[2',3'-5,6]pyrimido[3,4-a]-1,2,4-triazole;

5-ethylthio-10,10-dimethyl-tetrahydropyrano[3",4"-4',5']thieno[2',3'-5,6]pyrimido[3,4-a]-1,2,4-triazole;

5-ethylthio-9,10-dimethoxy-cyclohexothieno[2',3-5,6]pyrimido[3,4-a]-1,2,4-triazole;

3-isopropyl-5-(ethylthio)-cyclohexothieno[2',3'-5,6]pyrimido[3,4-a]-1,2,4-triazole;

3-isopropyl-5-ethylthio-piperido[3",4"-4',5']thieno[2',3'-5,6]pyrimido[3,4-a]-1,2,4-triazole;

3-isopropyl-5-ethylthio-10,10-dimethyl-tetrahydropyrano[3",4"-4',5']thieno[2',3'-5,6]pyrimido[3,4-a]-1,2,4-triazole;

3-isopropyl-5-ethylthio-9,10-dimethoxy-cyclohexothieno[2',3'-5,6]pyrimido[3,4-a]-1,2,4-triazole;

3-phenyl-5-(ethylthio)-cyclohexothieno[2',3'-5,6]pyrimido[3,4-a]-1,2,4-triazole;

3-phenyl-5-ethylthio-piperido[3",4"-4', 5']thieno[2',3'-5,6]pyrimido[3,4-a]-1,2,4-triazole;

3-phenyl-5-ethylthio-10,10-dimethyl-tetrahydropyrano[3",4"-4',5']thieno[2',3'-5,6]pyrimido[3,4-a]-1,2,4-triazole;

3-phenyl-5-ethylthio-9,10-dimethoxy-cyclohexothieno[2',3'-5,6]pyrimido[3,4-a]-1,2,4-triazole;

3-methyl-5-(butylthio)-cyclohexothieno[2',3'-5,6]pyrimido[3,4-a]-1,2,4-triazole;

3-methyl-5-butylthio-piperido[3",4"-4',5']thieno[2',3'-5,6]pyrimido[3,4-a]-1,2,4-triazole;

3-methyl-5-butylthio-10,10-dimethyl-tetrahydropyrano[3",4"-4',5']thieno[2',3'-5,6]pyrimido[3,4-a]-1,2,4-triazole;

3-methyl-5-butylthio-9,10-dimethoxy-cyclohexothieno[2',3'-5,6]pyrimido[3,4-a]-1,2,4-triazole;

5-butylthio-cyclohexothieno[2',3'-5,6]pyrimido[3,4-a]-1,2,4-triazole;

5-butylthio-piperido[3",4"-4',5']thieno[2',3'-5,6]pyrimido[3,4-a]-1,2,4-triazole;

5-butylthio-10,10-dimethyl-tetrahydropyrano[3",4"-4',5']thieno[2',3'-5,6]pyrimido[3,4-a]-1,2,4-triazole;

5-butylthio-9,10-dimethoxy-cyclohexothieno[2',3'-5,6]pyrimido[3,4-a]-1,2,4-triazole;

3-isopropyl-5-(butylthio)-cyclohexothieno[2',3'-5,6]pyrimido[3,4-a]-1,2,4-triazole;

3-isopropyl-5-butylthio-piperido[3",4"-4',5']thieno[2',3'-5,6]pyrimido[3,4-a]-1,2,4-triazole;

3-isopropyl-5-butylthio-10,10-dimethyl-tetrahydropyrano[3",4"-4',5']thieno[2',3'-5,6]pyrimido[3,4-a]-1,2,4-triazole;

3-isopropyl-5-butylthio-9,10-dimethoxy-cyclohexothieno[2',3'-5,6]pyrimido[3,4-a]-1,2,4-triazole;

3-phenyl-5-(butylthio)-cyclohexothieno[2',3'-5,6]pyrimido[3,4-a]-1,2,4-triazole;

3-phenyl-5-butylthio-piperido[3",4"-4',5']thieno[2',3'-5,6]pyrimido[3,4-a]-1,2,4-triazole;

3-phenyl-5-butylthio-10,10-dimethyl-tetrahydropyrano[3",4"-4',5']thieno[2',3'-5,6]pyrimido[3,4-a]-1,2,4-triazole;

3-phenyl-5-butylthio-9,10-dimethoxy-cyclohexothieno[2',3'-5,6]pyrimido[3,4-a]-1,2,4-triazole;

3-methyl-5-(benzylthio)-cyclohexothieno[2',3'-5,6]pyrimido[3,4-a]-1,2,4-triazole;

3-methyl-5-benzylthio-piperido[3",4"-4',5']thieno[2',3'-5,6]pyrimido[3,4-a]-1,2,4-triazole;

3-methyl-5-benzylthio-10,10-dimethyl-tetrahydropyrano[3",4"-4',5']thieno[2',3'-5,6]pyrimido[3,4-a]-1,2,4-triazole;

3-methyl-5-benzylthio-9,10-dimethoxy-cyclohexothieno[2',3'-5,6]pyrimido[3,4-a]-1,2,4-triazole;

5-benzylthio-cyclohexothieno[2',3'-5,6]pyrimido[3,4-a]-1,2,4-triazole;

5-benzylthio-piperido[3",4"-4',5']thieno[2',3'-5,6]pyrimido[3,4-a]-1,2,4-triazole;

5-benzylthio-10,10-dimethyl-tetrahydropyrano[3",4"-4',5']thieno[2',3'-5,6]pyrimido[3,4-a]-1,2,4-triazole;

5-benzylthio-9,10-dimethoxy-cyclohexothieno[2',3'-5,6]pyrimido[3,4-a]-1,2,4-triazole;

3-isopropyl-5-(benzylthio)-cyclohexothieno[2',3'-5,6]pyrimido[3,4-a]-1,2,4-triazole;

3-isopropyl-5-benzylthio-piperido[3",4"-4',5']thieno[2',3'-5,6]pyrimido[3,4-a]-1,2,4-triazole;

3-isopropyl-5-benzylthio-10,10-dimethyl-tetrahydropyrano[3",4"-4',5']thieno[2',3'-5,6]pyrimido[3,4-a]-1,2,4-triazole;

3-isopropyl-5-benzylthio-9,10-dimethoxy-cyclohexothieno[2',3'-5,6]pyrimido[3,4-a]-1,2,4-triazole;

3-phenyl-5-(benzylthio)-cyclohexothieno[2',3'-5,6]pyrimido[3,4-a]-1,2,4-triazole;

3-phenyl-5-benzylthio-piperido[3",4"-4',5']thieno[2',3'-5,6]pyrimido[3,4-a]-1,2,4-triazole;

3-phenyl-5-benzylthio-10,10-dimethyl-tetrahydropyrano[3",4"-4',5']thieno[2',3'-5,6]pyrimido[3,4-a]-1,2,4-triazole; and 3-phenyl-5-benzylthio-9,10-dimethoxy-cyclohexothieno[2',3'-5,6]pyrimido[3,4-a]-1,2,4-triazole.

Example 2

Activity (A) Yeast harboring an expression vector carrying the cDNA for wild-type PI3K catalytic subunit p110α grew in 2% glucose (uninduced), but PI3K expression caused growth inhibition when the cells were grown in 0.2–2% galactose (induced). The phenotype is noticeable by 24 hours and by 41.5 hours the effect is maximal. To ascertain whether the inhibitory effect of PI3K expression on yeast cell growth depends on its catalytic activity, a single mutation was generated in the conserved active site of the enzyme. Lysine was changed to an arginine at residue 802 (K802R). Yeast cells expressing the mutant constructs were not significantly different from vector-only controls. Thus, the growth inhibition observed in yeast requires the catalytically active form of PI3K. Furthermore, deletion of the CAAX box domain required for the proper localization of PI3K at the membrane also abolished the growth interference phenotype in yeast.

Yeast cell growth was severely inhibited whether PI3K was expressed episomally, or from a chromosomal locus. In our initial characterization of the growth phenotype caused by PI3K the protein was episomally expressed, but was integrated for compound screening.

(B) The protocol for the primary screen was as follows: SC-LEU (15 ml) with 2% glucose was inoculated from a frozen seed culture maintained at −80° C. The culture was grown overnight and washed once with SC-LEU media (no carbon source). The cells were diluted in the same medium containing 0.2% galactose and 2% raffinose to an OD600 of 0.02. This inoculum preparation (95 μl) was added to all the wells of 96-well assay plates, each containing 80 compounds in columns 2–11. Each compound (5 μl) was added at 100 μg/ml in 10% DMSO (final concentration in assay=5 μg/ml in 0.5% DMSO). Glucose was added to column 12 to a final concentration of 1% as positive growth control. Wells of column 1 contained the same cells and DMSO, but no compounds. The addition of compounds and cells to 96-well plates was carried out using a semi-automated Multimek pipeting station. The assay plates were incubated at 30° C. for 40–42 hours and OD600 was read. The percent growth rescue was calculated as 100 times the difference between the OD600 of the test well and the median of the wells in columns 2–11, divided by the difference between the median of the wells in column 12 and the median of the wells in columns 2–11. The median of the compound-containing wells served as an appropriate negative growth control value.

A library of compounds was screened. Compounds that provided at least 15% growth rescue were identified and confirmed by retesting, using compound freshly prepared, over a range of concentrations (0.25, 0.5, 1, 2, 4, 8, 16, 32, and 64 μM). These compounds were also tested for their effect on growth inhibition of vector-integrated yeast cells.

(C) Cytotoxicity: Mouse fibroblast cell line NIH-3T3 was used in the cytotoxicity assay of the confirmed "hit" compounds. The cells were cultured in DMEM medium containing 10% fetal bovine serum. The cells were seeded at 10,000 cells per well in 96-well plates and incubated at 37° C. overnight. Next morning, the medium in the plates was aspirated and replaced with 100 μl of freshly prepared medium containing various concentrations (0.03, 0.1, 0.3, 1, 3, 10, 30, and 90 μM) of the compounds (final DMSO= 0.3%). The plates were incubated for 48 hours or 72 hours at 37° C. Cell proliferation was determined using the MTS assay method.

(D) The compounds shown in the Table below demonstrated excellent potency. The therapeutic index was obtained by dividing the $CC_{50}$ values by $EC_{50}$ values for each compound.

What is claimed:

1. A compound of formula 1:

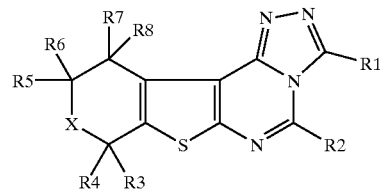

wherein X is O, or $NR_{11}$ (where $R_{11}$ is H or lower alkyl);

$R_1$ is lower alkyl, aryl, or aralkyl;

$R_2$ is methylthio, H, lower alkyl, aryl, aralkyl, heteroaryl, heteroaryl-alkyl, lower alkoxy, amino, lower alkylamino, lower acylamino, arylamino, arylacylamino, heteroaryl-amino, heteroaryl-acyl amino, thio, lower alkylthio, arylthio, or aralkyl-thio, where aryl and heteroaryl are substituted with 0–3 substituents selected from the group consisting of halo, trihalomethyl, hydroxy, lower alkyl and lower alkoxy;

$R_3$, $R_4$, $R_5$, $R_6$ $R_7$, and $R_8$ are each independently H, lower alkyl, lower alkoxy, or halo;

and pharmaceutically acceptable salts thereof.

2. The compound of claim 1, wherein $R_1$ is methyl.

3. The compound of claim 2, wherein X is O, $R_2$ is methylthio and $R_5$ and $R_6$ are each methyl.

| Structure | Compound | EC50 | CC50 | Index |
|---|---|---|---|---|
| 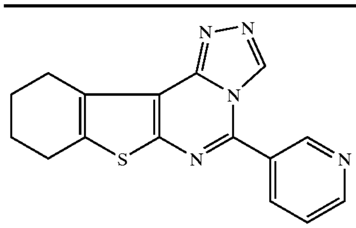 | 5-(3-pyridyl)-cyclohexo-thieno[2',3'-5,6]pyrimido-[3,4-a]-1,2,4-triazole | | | |
| 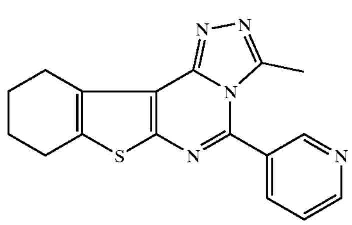 | 3-methyl-5-(3-pyridyl)-cyclohexothieno[2',3'-5,6]pyrimido[3,4-a]-1,2,4-triazole | | | |
| 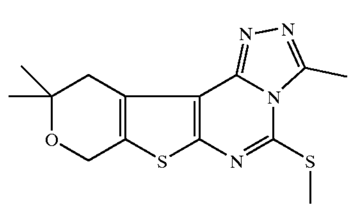 | 3,10,10-trimethyl-5-methylthio-tetrahydro-pyrano[3",4"-4',5']thieno-[2',3'-5,6]pyrimido[3,4-a]-1,2,4-triazole | | | |

4. A compound of formula:

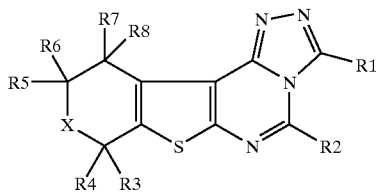

wherein X is $CR_9R_{10}$, $NR_{11}$ (where $R_9$ and $R_{10}$ are each independently H, lower alkyl, lower alkoxy, or halo, and $R_{11}$ is H or lower alkyl), or single bond;

$R_1$ is H, lower alkyl, aryl, or aralkyl;

$R_2$ is heteroaryl, heteroaryl-alkyl, lower alkoxy, amino, lower alkylamino, lower acylamino, arylamino, arylacyl-amino, heteroaryl-amino, heteroaryl-acyl amino, thio, lower alkylthio, arylthio, or aralkyl-thio, where heteroaryl is substituted with 0–3 substituents selected from the group consisting of halo, trihalomethyl, hydroxy, lower alkyl and lower alkoxy;

$R_3$, $R_4$, $R_5$, $R_6$, $R_7$, and $R_8$ are each independently H, lower alkyl, lower alkoxy, or halo;

and pharmaceutically acceptable salts thereof.

5. The compound of claim 4, wherein $R_3$, $R_4$, $R_7$, and $R_8$ are each H.

6. The compound of claim 5, wherein $R_2$ is 3-pyridyl, 4-pyridyl.

7. The compound of claim 6, wherein X is $CH_2$, and $R_5$ and $R_6$ are each H.

8. The compound of claim 7, wherein $R_1$ is H.

9. The compound of claim 7, wherein $R_1$ is methyl.

10. A composition for modulating the activity of a PI3 kinase, said composition comprising:

an effective amount of a compound of formula 1:

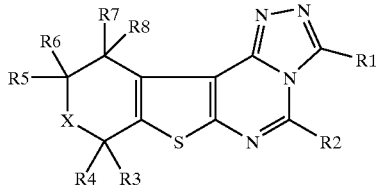

wherein X is $CR_9R_{10}$, $O$, $NR_{11}$ (where $R_9$ and $R_{10}$ are each independently H, lower alkyl, lower alkoxy, or halo, and $R_{11}$ is H or lower alkyl), or single bond;

$R_1$ is H, lower alkyl, aryl, or aralkyl;

$R_2$ is H, lower alkyl, aryl, aralkyl, heteroaryl, heteroaryl-alkyl, lower alkoxy, amino, lower alkylamino, lower acylamino, arylamino, arylacyl-amino, heteroaryl-amino, heteroaryl-acyl amino, thio, lower alkylthio, arylthio, or aralkyl-thio, where aryl and heteroaryl are substituted with 0–3 substituents selected from the group consisting of halo, trihalomethyl, hydroxy, lower alkyl and lower alkoxy;

$R_3$, $R_4$, $R_5$, $R_6$, $R_7$, and $R_8$ are each independently H, lower alkyl, lower alkoxy, or halo;

or a pharmaceutically acceptable salt;

and a pharmaceutically acceptable excipient.

11. A method for modulating the activity of a PI3 kinase, comprising:

contacting said PI3 kinase with an effective amount of a compound of formula 1:

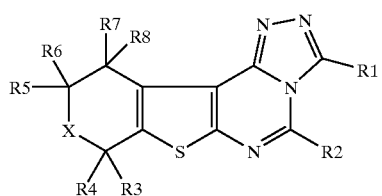

wherein X is $CR_9R_{10}$, $O$, $NR_{11}$ (where $R_9$ and $R_{10}$ are each independently H, lower alkyl, lower alkoxy, or halo, and $R_{11}$ is H or lower alkyl) or single bond;

$R_1$ is H, lower alkyl, aryl, or aralkyl;

$R_2$ is H, lower alkyl, aryl, aralkyl, heteroaryl, heteroaryl-alkyl, lower alkoxy, amino, lower alkylamino, lower acylamino, arylamino, arylacyl-amino, heteroaryl-amino, heteroaryl-acyl amino, thio, lower alkylthio, arylthio, or aralkyl-thio, where aryl and heteroaryl are substituted with 0–3 substituents selected from the group consisting of halo, trihalomethyl, hydroxy, lower alkyl and lower alkoxy;

$R_3$, $R_4$, $R_5$, $R_6$, $R_7$, and $R_8$ are each independently H, lower alkyl, lower alkoxy, or halo;

or a pharmaceutically acceptable salt thereof.

* * * * *